United States Patent [19]

Dvivedi et al.

[11] Patent Number: 4,569,825
[45] Date of Patent: Feb. 11, 1986

[54] PALLADIUM DENTAL ALLOY

[75] Inventors: Nitin N. Dvivedi, Covina; Paul A. Schmidt, Monrovia, both of Calif.

[73] Assignee: Unitek Corporation, Monroyia, Calif.

[21] Appl. No.: 641,138

[22] Filed: Aug. 15, 1984

[51] Int. Cl.$^4$ ................................................. C22C 5/04
[52] U.S. Cl. ..................................... 420/464; 433/207
[58] Field of Search ................. 420/464; 433/200, 207

[56] References Cited

U.S. PATENT DOCUMENTS

| | | | |
|---|---|---|---|
| 4,194,907 | 3/1980 | Tsai | 420/580 |
| 4,261,744 | 4/1981 | Boyajian | 433/207 |
| 4,336,290 | 6/1982 | Tsai | 433/207 |
| 4,350,526 | 9/1982 | Schaffer | 420/587 |

FOREIGN PATENT DOCUMENTS 3239338  2/1984  Fed. Rep. of Germany ...... 420/464

*Primary Examiner*—L. Dewayne Rutledge
*Assistant Examiner*—Robert L. McDowell
*Attorney, Agent, or Firm*—John J. Balser; Stuart E. Krieger; Richard H. Brink

[57] ABSTRACT

A palladium alloy suitable for use with both high and low thermal expansion dental porcelains without causing discoloration of the porcelains. The alloy consists essentially of 70-90% palladium, 1-8% silver, 0-5% gold, 5-16% copper, 1-8% gallium, 0.01-0.8% silicon and 0.001-0.5% grain refiners.

9 Claims, No Drawings

PALLADIUM DENTAL ALLOY

BACKGROUND OF THE INVENTION

1. Field of the Invention

The present invention relates generally to dental alloys and more particularly to a dental alloy suitable for use with both high and low thermal expansion porcelains.

2. Description of the Prior Art

Metallic alloys are commonly fused to dental porcelains for the fabrication of crowns, bridges and other prosthetic appliances. The various properties of these dental casting alloys are defined by the composition of the alloys. Such an alloy should exhibit an adequate balance of the following properties:

1. A coefficient of thermal expansion which makes the alloy suitable for use with commercially available porcelains.
2. Biocompatability with conditions in the mouth.
3. Good bonding characteristics with porcelains.
4. Ability to provide an aesthetically pleasing final product.
5. Characteristics enabling it to process well during casting.
6. Adequate strength and ductility.
7. Low cost.

For many years an adequate balance of these properties was obtained by using precious metals such as gold and platinum as primary elements in dental casting alloys. However, as the cost of precious metals increased, alternative alloy compositions were sought. As a result, cobalt and nickel based alloys became of great interest, but many of these alloys did not provide a satisfactory balance of properties with respect to the high degree of precision required during the casting step for some applications. Gold/palladium also became popular alternatives for use in dental castings. However, substantial and costly amounts of gold were still required to provide an adequate balance of properties.

With ever-increasing prices of gold, interest has turned to palladium-silver alloys. These alloys provide a reasonable balance of properties at a much lower cost than gold alloys. Yet, the use of palladium-silver alloys has not proven entirely satisfactory. For example, silver is known to cause greening of dental porcelains during the fusion process. One way of reducing the greening of the porcelains is to reduce the alloy's silver content and increase the alloy's palladium content, however, this method of reducing porcelain greening has been limited by the amount of palladium which can be used. For example, U.S. Pat. No. 4,350,526 states that a palladium content greater than 60% can adversely affect the overall balance of properties of the resulting palladium-silver alloy. U.S. Pat. Nos. 4,194,907 and 4,350,526 discuss the use of silicon in a palladium-silver alloy in order to prevent the silver from discoloring the porcelain, however, U.S. Pat. No. 4,261,744 indicates that more than 0.25% silicon in a high palladium content alloy can produce a cast product with crack and void defects.

Silver free palladium alloys have been proposed to avoid porcelain discoloration problems. Yet, these alloys have not been found entirely satisfactory either. For example, palladium is known to pick up gases during melting. This results in a porous casting which makes adhesion to dental porcelain difficult. U.S. Pat. No. 4,261,744 teaches that silicon can be used to prevent gas absorption in molten palladium, but, as previously mentioned, no more than 0.25% silicon can be incorporated in the alloy without producting castings with crack and void defects. In addition, palladium alloys tend to be compatible with only low thermal expansion porcelains; their compositions render then incompatible with high thermal expansion porcelains such as CRYSTAR TM.

SUMMARY OF THE INVENTION

Accordingly, it is an object of the present invention to provide a high palladium alloy which and provides a good balance of properties.

It is a further object of the present invention to provide a high palladium alloy containing silver which does not exhibit the adhesion problems resulting from gas absorption and which does not exhibit discoloration of the porcelain as a result of silver oxidation.

It is still a further object of this invention to provide a palladium alloy which is compatible with commercially available porcelains having high thermal expansion coefficients as well as porcelains having low thermal expansion coefficients.

These and other objects are attained by a palladium alloy which consists essentially of 70%–90% palladium, 1%–8% silver, 0%–5% gold, 5%–16% copper, 1%–8% gallium, 0.01%–0.8% silicon and 0.001%–0.5% of one or a combination of grain refiners selected from a group consisting of osmium, iridium, rhenium, rhodium and ruthenium, on a weight basis.

DETAILED DESCRIPTION

The alloy of the present invention utilizes palladium as its principle component. Copper and gallium are included to provide strength. Grain refiners are also included to provide the alloy with microfine grains.

The elemental constituents are alloyed by induction melting in ceramic crucibles. Carbon crucibles are not used to avoid contaminating the molten alloy. Carbon is dissolved by molten palladium and upon solidification it can cause embrittlement of the alloy. After the molten palladium alloy is homogenized, it is poured into a cast iron ingot mold. The ingot is rolled and sheared into flat, square coupons for remelting. Conventional dental laboratory techniques are used to fabricate test samples and finished restorations.

The alloy of the present invention should include preferably between 73%–79% palladium. However, as little as 70% and as much as 90% palladium can be used. The high palladium content alloy of this invention has been found to be compatible with low thermal expansion porcelains such as VITA TM VMK-68.

The alloy of this invention contains at least 1.0% silver and may contain as much as 8% silver. Amounts of silver above 8% should be avoided because it will increase porcelain greening during oxidation. Preferably the alloy of the present invention contains 2 to 6 percent silver. The incorporation of silver into this high palladium alloy makes the alloy compatible with high thermal expansion porcelains such as CRYSTAR TM. Alternatively, gold can be used to replace up to 5% of the silver. Preferably up to 2% gold is incorporated into the alloy of the current invention.

Copper and gallium are used to strengthen the alloy. Preferably the alloy contains 10% to 12% copper and 6% to 8% gallium. However, the alloy may contain as much as 16% copper and 8% gallium or as little as 5% copper and 1% gallium.

It was found that addition of between 0.01% to 0.8% silicon reduces both porcelain discoloration during baking cycles and the gas absorption of molten palladium during casting. Preferably, the alloy includes 0.1% to 0.5% silcon.

Finally, the alloy of this invention may contain one or a combination of grain refiners from a group comprising osmium, iridium, rhenium, rhodium, and ruthenium. Preferably, the alloy should include 0.05% to 0.3% grain refiners. However, the alloy may contain from 0.001% to no more than 0.5% grain refiners.

Alloys produced in accordance with the present invention were found to be compatible with commercially available high thermal expansion porcelains, such as CRYSTAR ™, and commercially available low thermal expansion porcelains, such as VITA ™ VMK-68. Typical properties of the alloy in this invention are as follows:

| | |
|---|---|
| Ultimate Tensile Strength | 100,000 psi |
| Yield Strength (0.2% offset) | 80,000 psi |
| Modulus of Elasticity | $18 \times 10^6$ psi |
| Elongation (1 inch gauge) | 15% |
| Hardness | 286 DPH |
| Coefficient of Thermal Expansion | $14.3 \times 10^{-6}$ in/in/°C. |
| Average Grain Size | 20 Microns |

The following examples further illustrate the invention but are not intended to be limiting. The figures shown are metal constituents in percentage by weight.

EXAMPLES

| | 1 | 2 | 3 | 4 | 5 |
|---|---|---|---|---|---|
| Palladium | 78.5 | 78.5 | 76.5 | 74.5 | 73.5 |
| Gold | 1.0 | — | — | — | 1.0 |
| Silver | 1.0 | 2.0 | 4.0 | 6.0 | 6.0 |
| Copper | 11.6 | 11.6 | 11.6 | 11.6 | 11.6 |
| Gallium | 7.5 | 7.5 | 7.5 | 7.5 | 7.5 |
| Silicon | 0.1 | 0.1 | 0.2 | 0.1 | 0.1 |
| Ruthenium | 0.2 | 0.2 | 0.2 | 0.2 | 0.2 |
| Osmium 0.1 | 0.1 | 0.1 | 0.1 | 0.1 | |
| Hardness (DPH) | 242 | 277 | 261 | 269 | 286 |

We claim:
1. An alloy consisting essentially of:

| | | |
|---|---|---|
| A. | 70–90% | palladium |
| B. | 0–5% | gold |
| C. | 1–8% | silver |
| D. | 5–16% | copper |
| E. | 1–8% | gallium |
| F. | 0.01–0.8% | silicon |
| G. | 0.001–0.5% | One or a combination of grain refiners selected from the group consisting of osmium, iridium, rhenium, rhodium and ruthenium. |

2. An alloy adapted for use with high and low thermal expansion dental porcelains consisting essentially of:

| | | |
|---|---|---|
| A. | 70–90% | palladium |
| B. | 0–5% | gold |
| C. | 1–8% | silver |
| D. | 5–16% | copper |
| E. | 1–8% | gallium |
| F. | 0.01–0.8% | silicon |
| G. | 0.001–0.5% | One or a combination of grain refiners selected from the group consisting of osmium, iridium, rhenium, rhodium and ruthenium. |

3. The alloy of claim 2 wherein said palladium content ranges from 73% to 79%.

4. The alloy of claim 2 wherein said silver content ranges from 2% to 6%.

5. The alloy of claim 2 wherein said gold content ranges from 0% to 2%.

6. The alloy of claim 2 wherein said copper content ranges from 10% to 12%.

7. The alloy of claim 2 wherein said gallium content ranges from 6% to 8%.

8. The alloy of claim 2 wherein said silicon content ranges from 0.1% to 0.5%.

9. The alloy of claim 2 wherein said grain refiner content ranges from 0.05% to 0.3%.

* * * * *